(12) United States Patent
Razifar et al.

(10) Patent No.: US 8,526,701 B2
(45) Date of Patent: Sep. 3, 2013

(54) IMAGE ANALYSIS METHOD AND SYSTEM

(75) Inventors: Pasha Razifar, Uppsala (SE); Bengt Langstrom, Uppsala (SE)

(73) Assignee: GE Healthcare Limited, Amersham (GB)

( * ) Notice: Subject to any disclaimer, the term of this patent is extended or adjusted under 35 U.S.C. 154(b) by 110 days.

(21) Appl. No.: 13/265,547

(22) PCT Filed: May 12, 2010

(86) PCT No.: PCT/US2010/034477
§ 371 (c)(1),
(2), (4) Date: Oct. 21, 2011

(87) PCT Pub. No.: WO2010/132523
PCT Pub. Date: Nov. 18, 2010

(65) Prior Publication Data
US 2012/0045106 A1    Feb. 23, 2012

Related U.S. Application Data

(60) Provisional application No. 61/177,374, filed on May 12, 2009.

(51) Int. Cl.
*G06K 9/00* (2006.01)
*G01T 1/164* (2006.01)
(52) U.S. Cl.
USPC ............. 382/131; 382/274; 250/363.03
(58) Field of Classification Search
USPC ......... 382/100, 103, 106, 128–134, 155, 382/162, 168, 173, 181, 232, 254, 255, 260, 382/274, 276, 305, 312; 250/363.03; 378/21, 378/2
See application file for complete search history.

(56) References Cited

U.S. PATENT DOCUMENTS

| 7,381,959 B2 * | 6/2008 | Manjeshwar et al. ... 250/363.03 |
| 8,175,360 B2 * | 5/2012 | Razifar et al. ................ 382/131 |
| 2008/0279436 A1 * | 11/2008 | Razifar et al. ................ 382/131 |
| 2010/0135556 A1 * | 6/2010 | Razifar et al. ................ 382/131 |

FOREIGN PATENT DOCUMENTS

| WO | 2007026231 | 3/2007 |
| WO | 2008050226 | 5/2008 |

OTHER PUBLICATIONS

Lukic A Set Al: "Effect of Spatial Alignment Transformations in PCA and ICA of Functional Neuroimages" IEEE Transactions on Medical Imaging, IEEE Service Center, Piscataway, NJ, US LNKD DOI: 10.1109/TM1.2007.896928, vol. 26, No. 8, Aug. 1, 2007 p. 1058-1068.*

(Continued)

*Primary Examiner* — Seyed Azarian
(74) *Attorney, Agent, or Firm* — Robert F. Chisholm

(57) ABSTRACT

The invention relates to a system and method for enhancing image data obtained from a positron emission tomography (PET) scan. In various embodiments, the method comprises transforming an original image data set to provide a first modified image data set by performing a masked volume-wise principal component analysis (MVW-PCA) on the original image data set. The first modified image data set is then transformed to provide a second modified image data set by performing a masked volume-wise independent component analysis (MVW-ICA) on the first modified image data set, the second modified image data set thereby comprising enhanced image data.

8 Claims, 7 Drawing Sheets

(56) References Cited

OTHER PUBLICATIONS

Lee J S et al: "Robust Extraction of Input Function From $H_2{}^{15}O$ Dynamic Myocardial Positron Emission Tomography Using Independent Component Analysis" Nuclear Science Symposium, 1999. Conference Record. 1999 IEEE Oct. 24-30, 1999, PiSCATAWAY, NJ, USA, IEEE, US LNKD DOI: 10.1109/NSSMIC. 1999.845828, vol. 2, Oct. 24, 1999, p. 990-994.

Lukic A S et al: "Effect of Spatial Alignment Transformations in PCA and ICA of Functional Neuroimages" IEEE Transactions on Medical Imaging, IEEE Service Center, Piscataway, NJ, US LNKD DOI: 10.1109TMI.2007.896928, vol. 26, No. 8, Aug. 1, 2007 p. 1058-1068.

PCT/US2010/034477 ISRWO Sep. 2, 2010.

\* cited by examiner

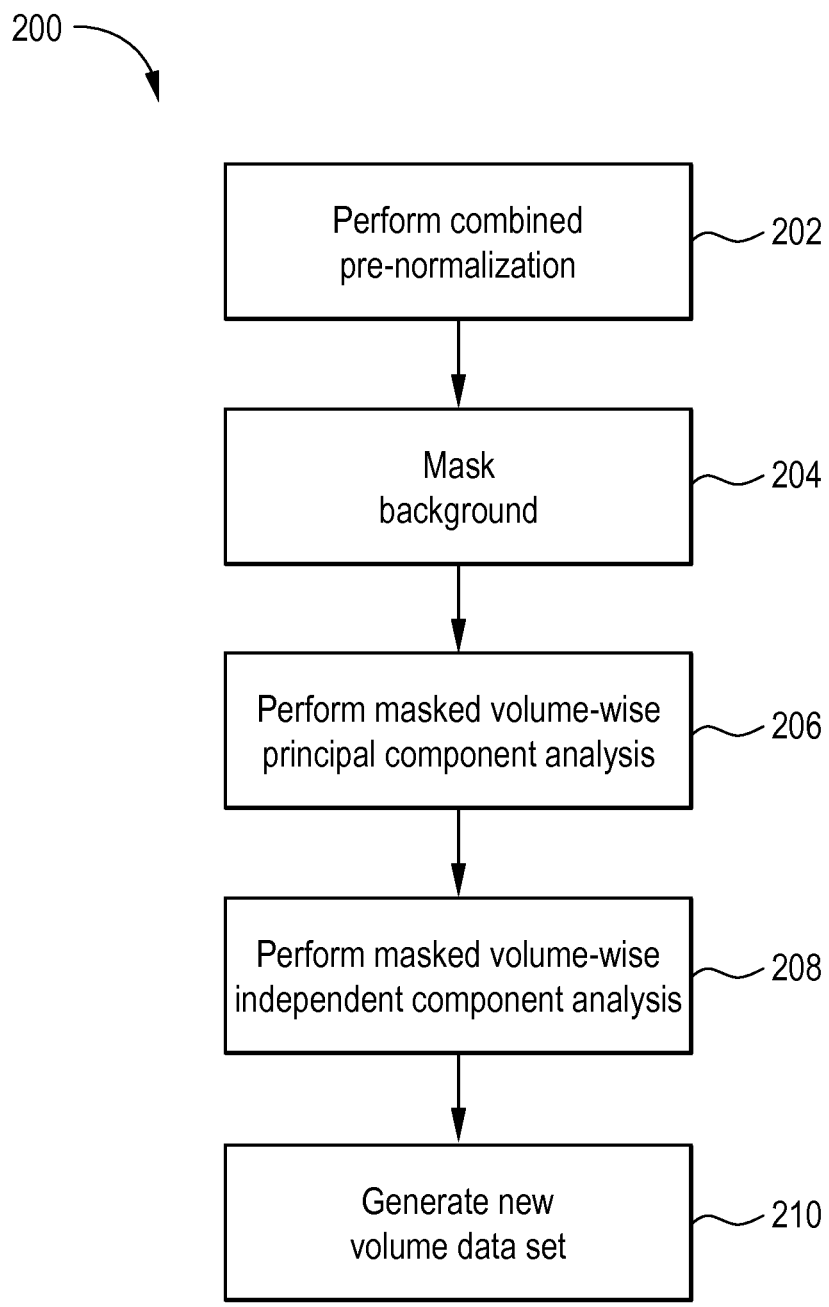

IMAGE ANALYSIS METHOD AND SYSTEM

This application is a filing under 35 U.S.C. 371 of international application number PCT/US2010/034477, filed May 12, 2010, which claims priority to U.S. application No. 61/177,374 filed May 12, 2009, the entire disclosure of which is hereby incorporated by reference.

FIELD OF THE INVENTION

The present invention generally relates to image analysis. In particular, the present invention relates to methods and apparatus for enhancing image data obtained from a positron emission tomography (PET) scan, including computer tomography (CT) images from combined PET/CT studies.

BACKGROUND OF THE INVENTION

Various medical imaging techniques exist to aid clinicians in the diagnosis of pathological conditions caused, for example, by anatomic or functional manifestations of a disease. Many such techniques produce one or more image frames that can be used to highlight to the clinician various instantaneous or temporal variations in anatomical and/or functional properties of a patient.

For example, PET imaging may be used to obtain a sequence of image frames showing, for example, how the physiological functional properties of a patient's organs, such as, for example, the brain, vary over time. See, e.g., S. R. Cherry, J. A. Sorenson, M. E. Phelps, Physics in Nuclear Medicine (3rd Edition), W.B. Saunders Co., ISBN-10: 072168341X, ISBN-13: 9780721683416, August 2003

PET is a known imaging technique that uses tomography to computer-generate a two- or three-dimensional image or map of a functional process in the body as a result of detecting gamma rays when artificially introduced radionuclides incorporated into biochemical substances decay and release positrons. Analysis of the photons detected from the annihilation of these positrons is used to generate the tomographic image frames which may be quantified using a colour scale to show the diffusion of the biochemical substances in the tissue thereby indicating localization of metabolic and/or physiological processes.

For example, radionuclides used in PET may be a short-lived radioactive isotopes such as flourine-18, oxygen-15, nitrogen-13, and carbon-11 (with half-lives ranging from about 110 minutes to about 20 minutes). The radionuclides may be incorporated into biochemical tracer substances such as compounds normally used by the body that may include, for example, sugars, water, and/or ammonia. The tracers may then be injected or inhaled into the body (e.g. into the blood stream) where the substance (e.g. a sugar) becomes concentrated in the tissue of interest, and where the radionuclides decay by emitting positrons. These positrons collide with nearby electrons producing gamma ray photons which can be detected and recorded thereby indicating where the radionuclide was taken up by the body. This set of data may be used to explore and depict one or more of anatomical, physiological, and metabolic information in the human body.

Although many tracers are currently used in PET studies to good effect, where various different tracers are used, e.g. for comparative studies of the same anatomical region, their differing biochemical properties can give rise to false indications of metabolic information for a particular organ.

For example, two different tracers might have different binding properties in a particular organ, respectively favoring binding to different tissue types. Additionally, or alternatively, different tracers might have different permeation rates across a particular membrane, such as the blood-brain boundary (BBB), for example.

Hence, when using various tracers, data analysis is more difficult and clinicians' attention might not be accurately drawn to the most clinically important organs, or regions of organs, since, for example, tissues or vessels surrounding them may show a higher tracer uptake than those more clinically significant areas.

There therefore exists a need for an improved imaging technique in which the most clinically significant features can be more reliably extracted for highlighting to clinicians, for example.

SUMMARY OF THE INVENTION

Various aspects and embodiments of the present invention have thus been devised whilst bearing in mind the aforementioned problems and disadvantages associated with conventional techniques.

According to a first aspect of the present invention, there is provided a method for enhancing image data obtained from a PET scan. The PET scan may produce image data from PET and/or PET/CT scans. The method comprises transforming an original image data set to provide a first modified image data set by performing a masked volume-wise principal component analysis (MVW-PCA) on the original image data set. The method also comprises transforming the first modified image data set to provide a second modified image data set by performing a masked volume-wise independent component analysis (MVW-ICA) on the first modified image data set.

According to a second aspect of the present invention, there is provided a computer program product comprising computer code for configuring a data processing apparatus to implement one or more of the steps of a method according to the first aspect of the present invention. Such a computer program product may be used to enhance or upgrade the functionality of conventional image processing or analysis apparatus to provide improved image analysis functionality.

According to a third aspect of the present invention, there is provided a system for enhancing image data obtained from a PET scan. The system comprises an image acquisition module and an image analyser. The image acquisition module is operable to acquire sinogram data derived from the PET scan in order to generate an original image data set. The image analyser is operable to transform the original image data set to provide a first modified image data set by performing a masked volume-wise principal component analysis on the original image data set, and to transform the first modified image data set to provide a second modified image data set by performing a masked volume-wise independent component analysis on the first modified image data set.

Second modified image data sets produced in accordance with various aspects of the present invention contain enhanced image data in which clinically significant features are more easily seen compared to corresponding image data sets produced using conventional techniques.

BRIEF DESCRIPTION OF THE DRAWINGS

FIG. 2 shows a method for enhancing an image according to various embodiments of the present invention;

DETAILED DESCRIPTION OF THE PREFERRED EMBODIMENTS

Figure 1:
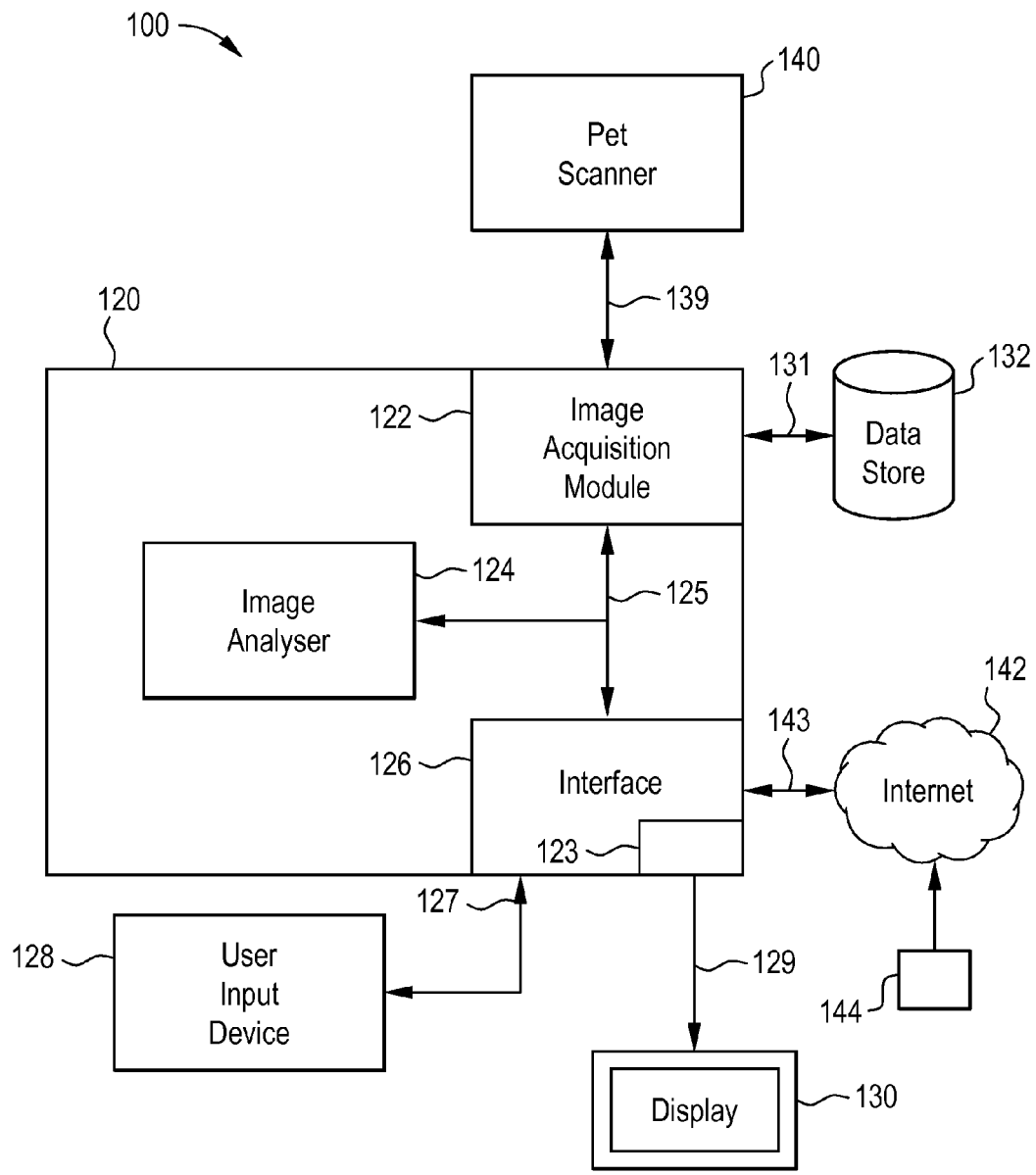
FIG. 1 shows a system for aiding clinical diagnosis of a subject according to an embodiment of the present invention.

FIG. 1 shows a system 100 for aiding clinical diagnosis of a subject according to an embodiment of the present invention. The system 100 includes a data processing apparatus 120 that is configured to provide various interfaces 123,126, an image acquisition module 122 and an image analyser 124. The interfaces 123,126, image acquisition module 122 and image analyser 124 can be logically coupled together by way of a data bus 125 under the control of a central processing unit (not shown).

The data processing apparatus 120 provides a first general purpose interface 126 for interfacing the data processing apparatus 120 to external components. In this embodiment the external components include: an input data link 127 coupled to at least one user input device 128 (e.g. a mouse/keyboard/etc.), a network data link 143 coupled to the Internet 142, and a display data link 129 coupled to a display 130. Additionally, the general purpose interface 126 also provides a GUI 123 through which a user of the system 100 can input data, commands etc., and receive visual information by viewing the display 130.

The GUI 123 may be operable to generate a two-dimensional and/or three-dimensional representation of various anatomical portions of the subject. Such representations may, for example, include colour coding of regions according to uptake or use of a substance in respective of those regions. This provides ease of visualisation for users of the system 100. In addition, in various embodiments, a user can also rotate images and/or slice 3D images by manipulating the GUI 123 using the input device 128.

In various embodiments, the data processing apparatus 120 can be provided by a general purpose computer, such as, for example, a personal computer (PC). Such a general purpose computer can use software modules to provide both the image acquisition module 122 and the image analyser 124, and hence can be implemented by upgrading the functional capability of existing equipment using software upgrades. For example, a computer program product 144, comprising computer code, may be transmitted from a remote server (not shown) via the Internet 142 to the data processing apparatus 120 through the network data link 143 or may be provided on a physical medium, such as, for example, a CD, DVD, magnetic disk, ROM, flash memory device, etc.

The system 100 also comprises an optional positron emission tomography (PET) scanner 140 coupled to the data processing apparatus 120 by a data link 139, and an optional data store 132 coupled to the data processing apparatus 120 by a data link 131. The PET scanner 140 and/or the data store 132 may be configured to provide image data to the image acquisition module 122. For example, where no PET scanner is provided, image data could be provided from the data store 132 that may contain previously generated image data stored therein. Such previously generated image data could be generated remotely from the system 100 (e.g. in a remote hospital, etc. where suitable image data generation facilities are available), and subsequently transferred to the data store 132 from where it can be retrieved by the image acquisition module 122. The image acquisition module 122 is further operable to transfer image data generated by the PET scanner 140 to the data store 132 for archiving purposes.

The image analyser 124 is operable to perform image analysis on image data. Such image data can be provided in the form of sinogram or raw image data, corresponding, for example, to a temporal sequence of images derived from a certain portion of a subject's anatomy. For example, the images may correspond to a time sequence of images showing the uptake of a radio-isotope tagged molecule in a subject's brain, heart, etc. derived from a PET scan. Alternatively, or in addition, the image frames may be derived from CT images of combined PET/CT studies.

FIG. 2 shows a method 200 for enhancing an image according to various embodiments of the present invention. The method 200 might, for example, be implemented by using a system 100 of the type shown in FIG. 1, and/or may be fully or partially automated to minimise or substantially eliminate the need for expert or non-expert user input.

The method 200 comprises a first optional step 202 of performing a combined pre-normalisation of sinogram data corresponding to an object, such as, for example, a subject's brain. This step 202 may be performed by using one or more of the techniques described by Razifar et al [See P. Razifar, Novel Approaches for Application of Principal Component Analysis on Dynamic PET Images for Improvement of Image Quality and Clinical Diagnosis, PhD thesis, Centre for Image Analysis, Uppsala University, Sweden, 2005, ISBN 91-554-6397-8; and P. Razifar, J. Axelsson, H. Schneider, B. LÅangstrom, E. Bengtsson, M. Bergström, A new application of pre-normalized principal component analysis for improvement of image quality and clinical diagnosis in human brain PET studies—Clinical brain studies using [$^{11}$C]-GR205171, [$^{11}$C]-L-deuterium-deprenyl, [$^{11}$C]-5-Hydroxy-L-Tryptophan, [$^{11C}$]-L-DOPA and Pittsburgh Compound-B, NeuroImage, Vol. 33(2), pp. 588-598, Elsevier Epub PMID: 16934493, 24 Aug. 2006, the entire contents of which, where permitted, are incorporated herein by reference as if disclosed here in their entirety], and is useful for reducing noise components in the sinogram data.

A second optional step 204 may then be performed to mask background data of the pre-normalised sinogram data. This further reduces noise in the image data leading ultimately to an improved image data set. Various techniques can also be used to implement this step 204, including, for example, those described by Razifar et al.

Having masked the background data of the pre-normalised sinogram data, a masked volume-wise principal component analysis is applied to the resultant data set at step 206. In this embodiment, the whole volume of the object is used as a single variable when applying the MVW-PCA, for example, using the techniques described by Razifar et al [infra, and also P. Razifar, J. Axelsson, H. Schneider, B. LÅngström, E. Bengtsson, M. Bergström, Volume-Wise Application of Principal Component Analysis on Masked Dynamic PET Data in Sinogram Domain, IEEE Transactions on Nuclear Medicine, Vol. 53(5), pp. 2759-2768, ISSN 0018-9499, 2006, WO 2007/026233, assigned to Healthcare Limited; and WO 2007/

026234, assigned to GE Healthcare Limited, the entire contents of which, where permitted, are incorporated herein by reference as if disclosed here in their entirety]. As a result, an original image data set corresponding to the object is transformed to provide a first modified image data set.

In one method for applying PCA, for example as described by Smith [See, Lindsay I Smith, A tutorial on Principal Components Analysis, 26 Feb. 2002, http://www.cs.otago.ac.nz/cosc453/student_tutorials/principal_components.pdf; the entire contents of which, where permitted, are incorporated herein by reference as if disclosed here in their entirety], a covariance matrix $C^{n \times n}$ for a data set having n dimensions is calculated, as follows:

$$\text{cov}(X, Y) = \frac{\sum_{i=1}^{N}(X_i - \overline{X})(Y_i - \overline{Y})}{N} \quad (1)$$

where covariance is measured between two dimensions, where $X_i$ is the $i^{th}$ data point in the X dimension, $\overline{X}$ is the mean value of all the data in the X dimension, N is the total number of data points in the X dimension and cov(X,Y) is the covariance measured between the X and Y dimensions.

Using equation (1) a covariance matrix can be built up using pairs of data in two dimensions to define the covariance matrix C for a set of data with n dimensions as:

$$C^{n \times n} = (c_{i,j}, c_{i,j} = \text{cov}(\text{Dim}_i, \text{Dim}_j)) \quad (2)$$

with $\text{Dim}_x$ being the $x^{th}$ dimension. For example, where a three dimensional data set is provided, having dimensions x, y and z, n=3 and the covariance matrix C has three rows and three columns, and is defined as:

$$C = \begin{pmatrix} \text{cov}(x, x) & \text{cov}(x, y) & \text{cov}(x, z) \\ \text{cov}(y, x) & \text{cov}(y, y) & \text{cov}(y, z) \\ \text{cov}(z, x) & \text{cov}(z, y) & \text{cov}(z, z) \end{pmatrix} \quad (3)$$

Having determined the covariance matrix C, unit eigenvectors for that covariance matrix C are then determined in a conventional manner [Lindsay I Smith, A tutorial on Principal Components Analysis, 26 Feb. 2002, http://www.cs.otago.ac.nz/cosc453/student_tutorials/principal_components.pdf; R. C. Gonzalez and R. E. Woods, Digital Image Processing, Addison Wesley Publishing Company, 1992, the contents of which, where permitted, are incorporated by reference herein as if disclosed here in their entirety].

The unit eigenvectors thus determined are ordered according to their respective eigenvalues, starting from the eigenvector having the highest eigenvalue (i.e. the most significant component, PC1) and moving to the eigenvector having the lowest eigenvalue (i.e. the least significant component, PCn). The eigenvectors thus ordered PC1-PCn therefore provide a set of n eigenvectors corresponding to the principal components of the image data set for the object.

The first modified image data set produced by step 206 is then transformed by the application of masked volume-wise independent component analysis to a second modified image data set at step 208. In various embodiments of the present invention various of the techniques referred to below [See, e.g., P. Common, Independent Component Analysis—A New Concept?, Signal Processing, Vol. 36, pp. 287-314, 1994; A. Hyvarinen, Fast and Robust Fixed-Point Algorithms for Independent Component Analysis, IEEE Transactions on Neural Networks, Vol. 10(3), pp. 626-634, 1999; A. Hyvärinen, Survey on Independent Component Analysis, Neural Computing Surveys, Vol. 2, pp. 94-128, 1999; A. Hyvärinen and E. Oja, Independent Component Analysis Algorithms and Applications, Neural Networks, Vol. 13(4-5), pp. 411-430, 2000, the contents of which, where permitted, are incorporated by reference herein as if disclosed here in their entirety] may be used to generate the second modified image data set.

One advantage of various embodiments of the present invention lies in the synergy provided by combining both MVW-PCA and MVW-ICA techniques. For example, MVW-PCA is a technique that can be used for signal separation and improvement of image quality and MVW-ICA's strength is based on enhanced signal extraction. Thus by performing MVW-PCA we are able to improve image quality and separate tissues with different kinetic behaviours into different principal components.

However sometimes when dealing with tracers that do not easily pass the BBB, for example, various tissues with the same kinetic behaviours are separated into the same principal components. So by using the MVW-ICA technique, it is then possible separate signals from tissues with same kinetic behaviour from each other and separate them further in two new components. By doing this it is therefore possible to separate tissues with same kinetic behaviour into different components for further analysis.

This, for example, makes it possible to study the uptake of tracer in small sized tissues or in tissues with a low uptake of the administered tracer, a feat that is not easily achieved when using either MVW technique in isolation.

Having generated the second modified image data set, a further optional step 210 may be performed to generating a new data set by back-projecting the second modified image data onto a zero matrix. For example, the techniques described by Razifar et al [infra] may be used. The new data set may then be used to generate an image for displaying the object of interest to a user, for example, using a graphical user interface presented to the user via a display unit.

Figure 3B:
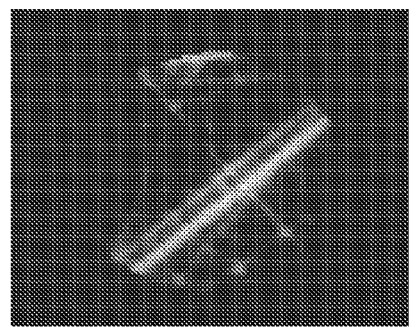
FIG. 3B shows an image showing artifact image components caused by non-calibrated detectors.
Figure 3A:
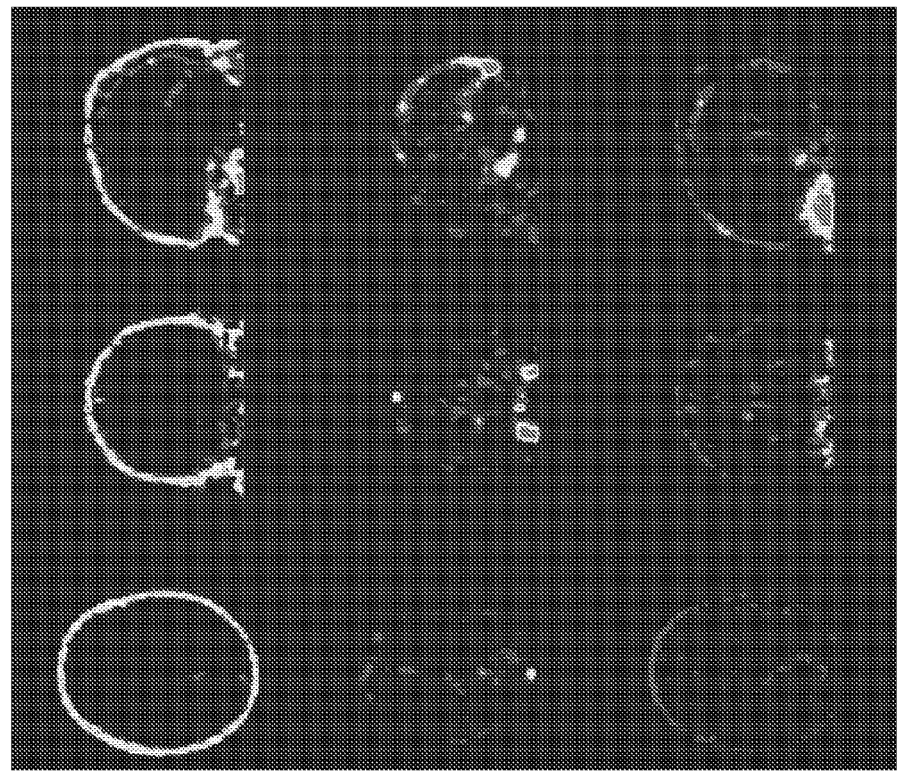
FIG. 3A shows a sequence of images showing improved signal separation in a brain image provided in accordance with a technique of the present invention.

FIG. 3A shows a sequence of images 300 showing improved signal separation in a brain image provided in accordance with a technique of the present invention. In the upper row of images a first axial image is shown towards the left hand side of the figure, followed by a first coronal image towards the row centre then by a first sagittal image to the right hand side of the figure. The central row comprises a second axial image, followed by a second coronal image then a second sagittal image. The bottom row comprises a third axial image, followed in the centre of the row by a third coronal image then a third sagittal image. Hence the first (left hand side) column of the sequence of images 300 comprises a sequence of three axial images, the second (central) column a sequence of three coronal images, and the third (right hand side) column a sequence of three sagittal images.

The images were derived from an original image data set that had been obtained as a result of a PET scan of a subject performed using an apoptosis marker. The subject was a stroke victim and the apoptosis marker was used to highlight areas affected by the stroke.

The original image data set was processed in accordance with a technique according to an aspect of the present invention wherein both MVW-PCA and MVW-ICA were applied (see FIG. 2 and the description above). The upper row comprises a first set of components obtained as a result of this technique, the middle row a second set of components obtained as a result of this technique, and the third row a third set of components obtained as a result of this technique.

FIG. 3B shows an image 302. Image 302 includes a fourth set of components obtained as a result of the technique and shows artifact image components caused by non-calibrated detectors. Such components may usefully be employed to analyse and/or diagnose the performance of the PET scanner, for example, either as part of a manufacturing quality control process or during the operational lifetime of the scanner. Such an image 302 might thus be obtained routinely during scans, compared to previously archived images and used to automatically diagnose any significant degradation, e.g. that would require routine or urgent maintenance, in scanner performance over time.

Figure 4A:
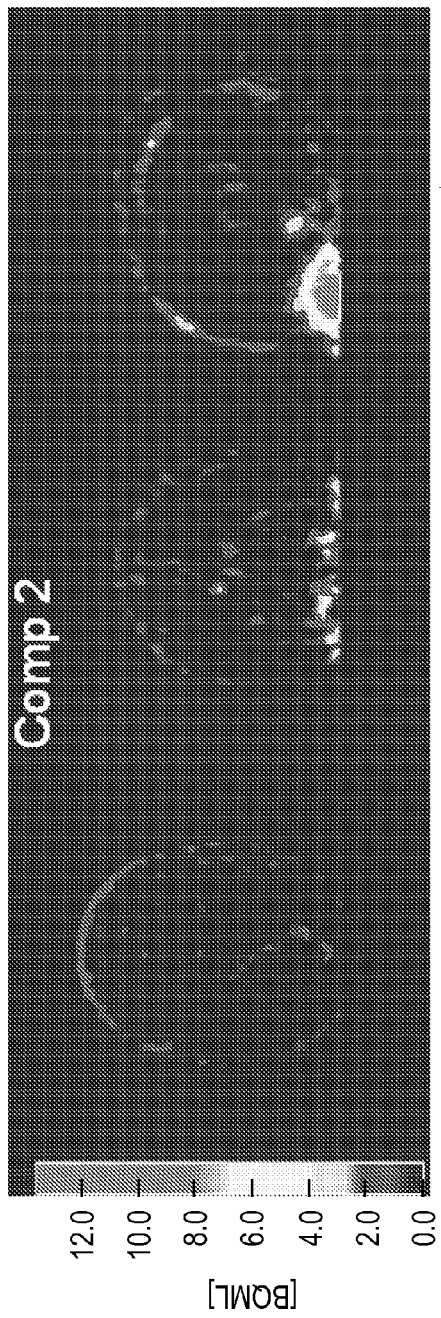
FIG. 4A shows a sequence of images showing a view of the bottom row of the sequence of images shown in FIG. 3A.

FIG. 4A shows a sequence of images 400 showing a view of the bottom row (labelled Comp 2) of the sequence of images 300 shown in FIG. 3A. The scale at the left hand side of FIG. 4A adjacent the (third) axial image indicates uptake of the apoptosis marker in units of Becquerels per millilitre (Bq/ml). The right hand (third) sagittal image clearly shows a large bright region of high marker uptake in its lower left area indicating that substantial stroke damage has been sustained towards the front of the subject's brain.

Figure 4B:
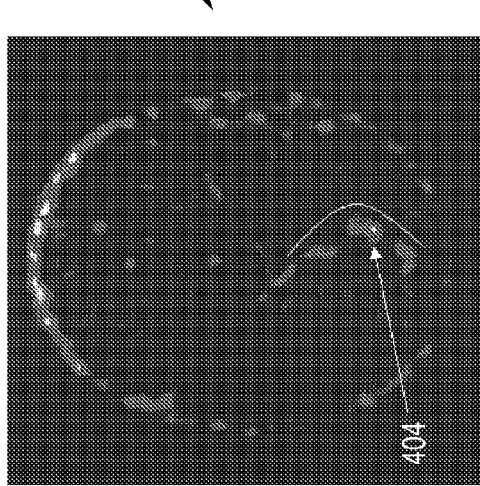
FIG. 4B shows an image showing the axial view of the images of FIG. 4A in enlarged view.

FIG. 4B shows an image 402 showing the axial view of the images 400 of FIG. 4A enlarged. Whilst the major stroke damage shown in the third sagittal view could be detected using conventional techniques, the image 402 reveals more subtle features 404 that can readily be revealed in vivo by using the Applicant's new technique.

The features 404 indicate an area where the marker has been taken up. The line in image 402 indicates a path along which the marker has been taken up. The features 404 and line indicate clinically significant areas in which either stroke damage has occurred and/or where BBB has been destroyed.

Figure 5A:
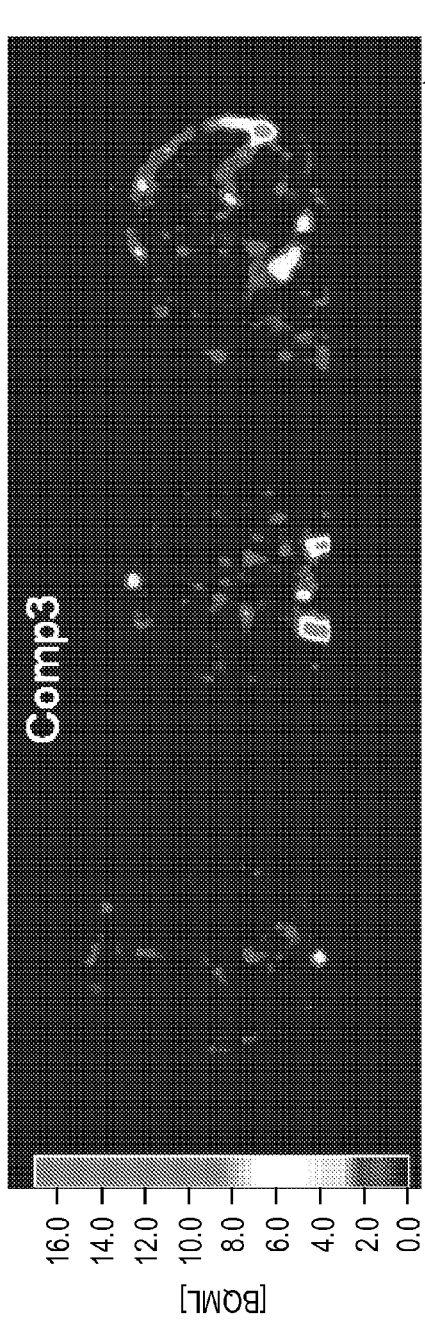
FIG. 5A shows a sequence of images showing a view of the middle row of the sequence of images shown in FIG. 3A.

FIG. 5A shows a sequence of images 500 showing a view of the middle row of the sequence of images shown in FIG. 3A (labelled Comp 3). The scale at the left hand side of FIG. 5A adjacent the (second) axial image indicates uptake of the apoptosis marker in units of Becquerels per millilitre (Bq/ml). The central (second coronal) and right hand (second sagittal) images clearly show two large bright regions of high marker uptake indicating where substantial stroke damage has been sustained.

Figure 5B:
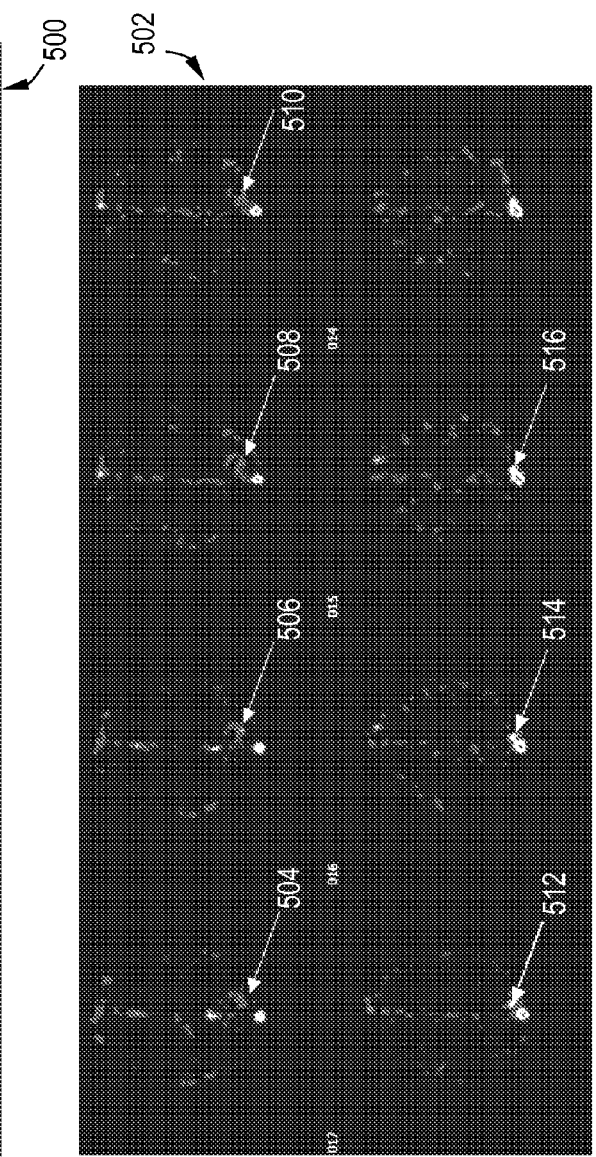
FIG. 5B shows a sequence of images showing various processed views of the axial image of FIG. 5A.

FIG. 5B shows a sequence of images 502 showing various processed views of the (second) axial image of FIG. 5A. The sequence of images 502 clearly shows features 504, 506, 508, 510, 512, 514 and 516 that were not visible before the application of the Applicant's new technique. These areas were not visible previously since uptake of the marker in blood vessels was highly dominant. However, application of the new technique enables these clinically significant features to be extracted and clearly presented for further assessment.

Figure 6A:
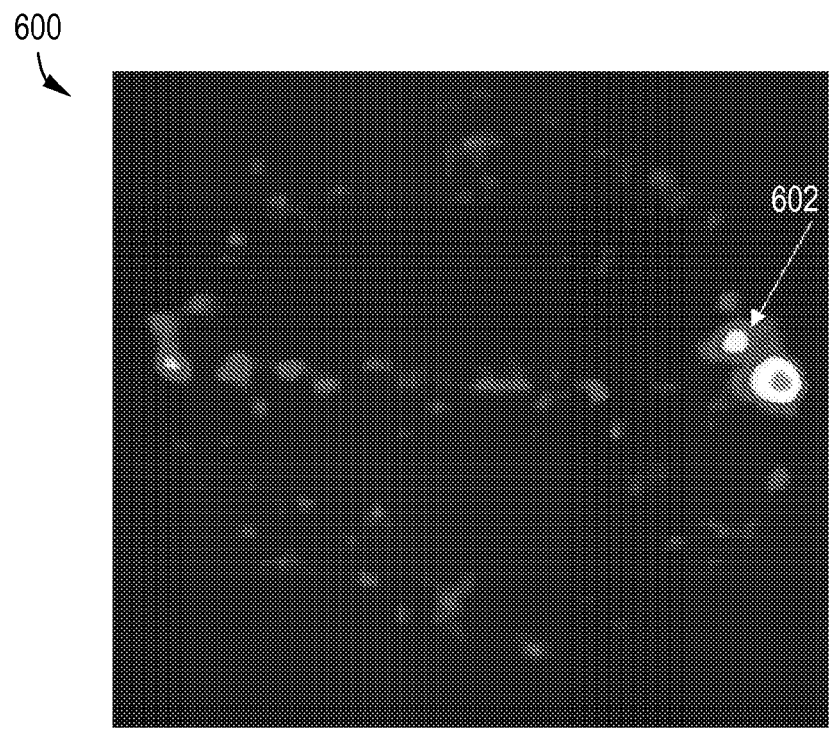
FIG. 6A shows an enlarged view of one of the images of FIG. 5B.

FIG. 6A shows an enlarged view 600 of one of the images including features 510 of FIG. 5B. The scaling factor applied has been modified so that the features 602 in image 600 are more clearly visible.

Figure 6B:
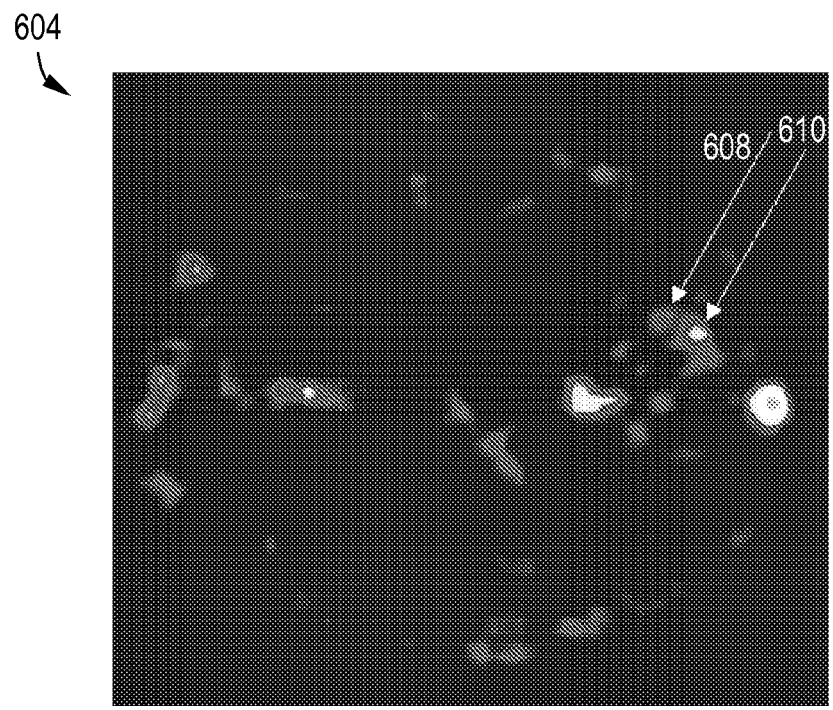
FIG. 6B shows an additional enlarged view of one of the images of FIG. 5B.

FIG. 6B shows an additional enlarged view 604 of one of the images including features 504 of FIG. 5B. Previously unseen clinically significant features 608 and 610 are clearly visible.

Figure 7:
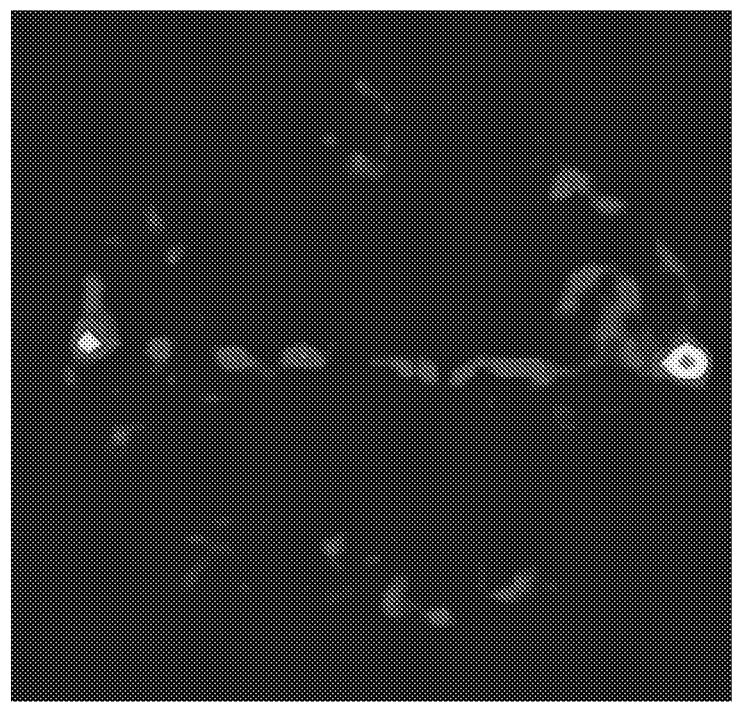
FIG. 7 shows another enlarged view of one of the images of FIG. 5B.

FIG. 7 shows another enlarged view 700 of one of the images including features 508 of FIG. 5B.

In summary, an apoptosis marker was used in order to illustrate the stroke area in brain tissue. However, this tracer has very high uptake in blood vessels of the brain and a low uptake in the stroke area. Hence, using conventional techniques, since the uptake in blood vessels is dominant, it is very difficult to determine the stroke area. However, as can be clearly seen from FIGS. 5A to 7, by applying various techniques in accordance with the present invention this issue can be addressed thus enabling the extraction of otherwise hidden clinically significant features.

Various embodiments of the present invention may be configured to provide automatic quantification of tracer uptake in various regions of a PET scan.

Certain embodiments of the present invention can also, or alternatively, provide a GUI to aid users in visualising small sized tissues, e.g. objects of interest, and to input regions of interest (ROI) using the GUI corresponding to those areas using an image separated into different components. Additionally, or alternatively, the ROIs may be imported with original activity data, e.g. sinogram data, to enable quantification measurements to be obtained. Certain GUI embodiments may enable users to scale 2-dimensional and/or 3-dimensional images up and/or down in order to visualise objects of interest more easily (e.g. by scaling a colour bar down).

Whilst the present invention has been described in accordance with various aspects and preferred embodiments, it is to be understood that the scope of the invention is not considered to be limited solely thereto and that it is the Applicant's intention that all variants and equivalents thereof also fall within the scope of the appended claims.

What is claimed is:

1. A method (200) for enhancing image data obtained from a positron emission tomography (PET) scan, the method comprising:
    transforming an original image data set to provide a first modified image data set by performing a masked volume-wise principal component analysis (MVW-PCA) (206) on the original image data set;
    transforming the first modified image data set to provide a second modified image data set by performing a masked volume-wise independent component analysis (MVW-ICA) (208) on the first modified image data set, and
    generating a new data set (210) from the second modified image data set by back-projecting the second modified image data onto a zero matrix.

2. The method (200) of claim 1, further comprising performing a combined pre-normalisation (202) operation on sinogram data derived from the PET scan in order to generate the original image data.

3. The method (200) of claim 1, further comprising masking a background (204) in the original image data.

4. A computer program product (144) stored on a non-transitory computer readable medium comprising computer code for configuring a data processing apparatus (120) to implement one or more of the steps (202, 204, 206, 208, 210) of the method (200) according to claim 1.

5. A system (100) for enhancing image data obtained from a positron emission tomography (PET) scan, the system (100) comprising:
    an image acquisition module (122) operable to acquire sinogram data derived from the PET scan in order to generate an original image data set; and
    an image analyser (124) operable to: a) transform the original image data set to provide a first modified image data set by performing a masked volume-wise principal component analysis (MVW-PCA) on the original image data set; and b) transform the first modified image data set to provide a second modified image data set by performing a masked volume-wise independent component analysis (MVW-ICA) on the first modified image data set, wherein the image analyser (124) is further configured to generate a new data set from the second modified image data set by back-projecting the second modified image data onto a zero matrix.

6. The system (100) of claim 5, wherein the image analyser (124) is further configured to perform a combined pre-normalisation operation on sinogram data derived from the PET scan in order to generate the original image data.

7. The system (100) of claim 5, wherein the image analyser (124) is further configured to mask a background in the original image data.

8. The system (100) of claim 5, further comprising a PET scanner (140) operably coupled to the image acquisition module (122).

\* \* \* \* \*